United States Patent [19]

Hsu et al.

[11] Patent Number: 4,522,757

[45] Date of Patent: Jun. 11, 1985

[54] PROCESS FOR OXIDIZING A PHENOL TO A P-BENZOQUINONE

[75] Inventors: Chao-Yang Hsu, Media; James E. Lyons, Wallingford, both of Pa.

[73] Assignee: Sun Tech, Inc., Philadelphia, Pa.

[21] Appl. No.: 527,892

[22] Filed: Aug. 30, 1983

Related U.S. Application Data

[63] Continuation-in-part of Ser. No. 436,492, Oct. 25, 1982, abandoned.

[51] Int. Cl.³ .................. C07C 45/16; C07C 49/64
[52] U.S. Cl. .................................................. 260/396 R
[58] Field of Search ............... 260/396 R, 687 R; 568/772

[56] References Cited

U.S. PATENT DOCUMENTS

| | | | |
|---|---|---|---|
| 3,210,384 | 11/1965 | Hay | 260/396 N |
| 3,870,731 | 3/1975 | Hutchings | 260/396 R |
| 3,987,068 | 10/1976 | Reilly | 260/396 R |
| 4,208,339 | 6/1980 | Costantini et al. | 260/396 R |
| 4,257,968 | 3/1981 | Reilly | 260/396 R |

OTHER PUBLICATIONS

Aarua et al., *Chemical Abstract*, vol. 55, #7333c, 1961, "Oxidation of Certain Phenols in an Alkaline Medium".

*Primary Examiner*—Glennon H. Hollrah
*Assistant Examiner*—Raymond Covington
*Attorney, Agent, or Firm*—J. Edward Hess; Donald R. Johnson; Stanford M. Back

[57] ABSTRACT

Phenol or a substituted phenol is oxidized to the corresponding benzoquinone or substituted benzoquinone in the presence of a copper halide or copper nitrate catalyst promoted with an oxide or hydroxide of a Group II metal.

17 Claims, No Drawings

PROCESS FOR OXIDIZING A PHENOL TO A P-BENZOQUINONE

This application is a continuation-in-part of application Ser. No. 436,492 filed Oct. 25, 1982, now abandoned.

BACKGROUND OF THE INVENTION

It is known in the art to oxidize phenol to p-benzoquinone with oxygen in the presence of a copper ion catalyst and such a process is disclosed in U.S. Pat. No. 3,987,068. In that patent the oxidation is carried out in a nitrile solvent using a complex formed from the copper catalyst and the solvent and the operating conditions are said to be at temperatures of from about 0° to 100° C. and a partial pressure of oxygen of from about 7 to 200 (preferably 14 to 100) atmospheres. As pointed out in U.S. Pat. No. 3,987,068, yield of quinone product increases with increased partial pressure of oxygen and it appears from the data therein that partial pressures of oxygen above about 100 atmospheres are required in order to achieve conversions of phenol to p-benzoquinone on the order of about 75%. Such pressures are too high to be useful in an economical commercial process because they require special equipment of high capital cost.

U.S. Pat. No. 4,208,339 discloses a process for the preparation of p-benzoquinone by oxidation of phenol in the presence of cuprous or cupric ions and in the presence of a metal in the metallic form in a nitrile, amide, alcohol or sulfoxide solvent. Reaction rate is said to be increased by including an alkali metal or alkaline earth metal halide.

SUMMARY OF THE INVENTION

It has now been found that the copper catalyzed process for oxidation of a phenol to p-benzoquinone or a substituted p-benzoquinone can be significantly improved so as to enable operation at lower, commercially useful pressures and still achieve an improved conversion and/or improved selectivity to product. In accord with the invention, such objectives are achieved by conducting the oxidation of a phenol in the presence of a copper ion catalyst which is promoted with an oxide or hydroxide of a Group II A metal; e.g., Be, Mg, Ca, Sr, Ba, etc.

DETAILED DESCRIPTION

According to the invention, phenol and substituted phenols are converted to corresponding p-benzoquinone and substituted p-benzoquinones as illustrated in the following reaction:

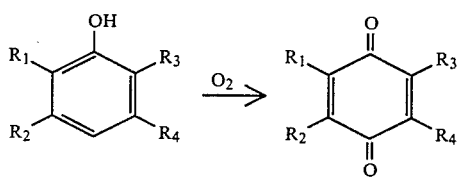

wherein $R_1$, $R_2$, $R_3$ and $R_4$ may be the same or different and may comprise hydrogen, halo or cyano, alkyl or alkoxy containing 1 to about 12 carbon atoms; phenyl, naphthyl, phenylalkyl, alkylphenyl, phenoxy or phenalkoxy, containing 7 to about 16 carbon atoms; and $R_1$ and $R_2$ or $R_3$ and $R_4$ may be joined to form an aliphatic, aryl or hetero ring. Specific R groups include chloro, cyano, methyl, ethyl, propyl, butyl, isobutyl, tert-butyl, pentyl, p-tolyl, p-anisyl, methoxy, t-butoxy, phenoxy, p-methylphenoxy, and the like. Preferred phenols useful in the process are phenol, o-chlorophenol, o-cresol, m-cresol, 2,5- and 2,6-di-t-butylphenol, 2-t-butylphenol, 2,6-dimethylphenol, and 1-naphthol. When $R_1$ and $R_2$ or $R_3$ and $R_4$ are joined, the resulting p-benzoquinones will be those derived from naphthalene, quinoline, isoquinoline, chroman (dihydrobenzopyran), indole and the like.

In carrying out the process of the invention, conventional temperature conditions, solvent systems and a monovalent or divalent (i.e., cuprous or cupric) copper catalyst may be used. Thus, a temperature of from about 20° to about 100° C. (preferably about 50° to 75° C.) and a nitrile solvent, preferably acetonitrile, is usually employed. The copper catalyst will preferably be a copper halide, preferably chloride, and preferably a monovalent copper catalyst. Copper nitrate is operable and mixtures of such salts also may be used. However, other copper II salts such as acetates, sulfates, benzoates, carbonates, phosphates, and bisulfates have been found not to be effective catalysts for the reaction. The mole ratio of phenol reactant to catalyst may vary widely, on the order of from about 50:1 to 1:1, preferably about 15:1 to 5:1. The Group II A oxide or hydroxide promoters will preferably be those of Be, Mg, and Ca. The amount of promoter to be used will generally be from about 0.1 to about 1.9 mole promoter per mole of catalyst; a mole ratio of about 1:1 has been found to be quite effective. As indicated above, the reaction can be carried out at moderate pressures and such pressures will generally be between about 100 and about 500 psig partial pressure of oxygen, preferably between about 200 and 400 psig. Mixtures of oxygen and nitrogen, air alone, or oxygen alone may be used, but preferably mixtures of oxygen and nitrogen such as air will be employed as the oxygenating medium.

In order to further illustrate the invention, the following examples are given:

EXAMPLE 1

A solution of phenol in 5 ml. of acetonitrile which was agitated in a magnetically stirred mini-autoclave under an initial total pressure of 750 psig was oxidized over a three hour period with a mixture of 40% (vol.) oxygen and 60% nitrogen in the presence of a CuCl or $CuCl_2$ catalyst. The reaction parameters and results obtained are shown in the following Table I.

TABLE I

EFFECT OF GROUP IIA OXIDES AND HYDROXIDES ON THE COPPER-CATALYZED OXIDATION OF PHENOL TO P-BENZOQUINONE

| Run No. | Cat. | M Mole Cat. | Promoter | M Mole Promoter | M Mole Phenol | Temp. (°C.) | Time (Min.) | PBQ Select. (%) | Phenol Conv. (%) | PBQ Yield (%) |
|---|---|---|---|---|---|---|---|---|---|---|
| 1 | $CuCl_2$ | 0.55 | — | — | 3.51 | 65 | 180 | 42 | 85 | 36 |
| 2 | $CuCl_2$ | 0.55 | BeO | 0.55 | 7.37 | 65 | 180 | 57 | 47 | 27 |
| 3 | $CuCl_2$ | 0.55 | CaO | 0.55 | 8.22 | 65 | 180 | 46 | 95 | 44 |
| 4 | $CuCl_2$ | 0.55 | $Ca(OH)_2$ | 0.55 | 7.39 | 65 | 180 | 44 | 94 | 40 |
| 5 | CuCl | 0.55 | — | — | 3.82 | 65 | 180 | 39 | 100 | 39 |
| 6 | CuCl | 0.55 | BeO | 0.55 | 7.46 | 65 | 180 | 61 | 89 | 55 |
| 7 | CuCl | 0.55 | BeO | 0.55 | 7.83 | 65 | 180 | 59 | 97 | 57 |
| 8 | CuCl | 0.55 | CaO | 0.55 | 8.22 | 65 | 180 | 57 | 94 | 54 |

As can be seen from the above data, significant improvements are obtained by use of the promoters. Thus, with divalent copper catalyst, in Run 2, the BeO promoter results in increased selectivity to p-benzoquinone (PBQ) although conversion and yield are low. With CaO and Ca(OH)$_2$, however, (Runs 3 and 4) significant improvements in conversion and yield over the control (Run 1) are achieved.

With the monovalent copper catalyst, both selectivity and yield of PBQ are significantly improved by use of the promoter (compare Runs 6, 7, and 8 with Run 5).

EXAMPLES 2–7

In experiments which may be conducted substantially as described in example 1, except for substitution of the substituted phenols listed below, good improvements in selectivity to the corresponding substituted benzoquinones, conversion and/or yield are achieved:

TABLE II

| Ex. No | Substituted phenol | Product |
|---|---|---|
| 2 | o-cresol | 2-methyl-p-benzoquinone |
| 3 | m-cresol | 2-methyl-p-benzoquinone |
| 4 | 2,6-dimethylphenol | 2,6-dimethyl-p-benzoquinone |
| 5 | 2,6-di-t-butylphenol | 2,6-di-tert-butyl-p-benzoquinone |
| 6 | o-t-butylphenol | 2,-tert-butyl-p-benzoquinone |
| 7 | 2,5-di-t-butylphenol | 2,5-di-tert-butyl-p-benzoquinone |

We claim:

1. In the process of oxidizing phenol or a substituted phenol to benzoquinone or a substituted benzoquinone with a copper salt catalyst selected from the group of halides and nitrates, the improvement which comprises promoting the catalyst with an oxide or hydroxide of a Group II A metal.

2. The process of claim 1 wherein the catalyst is cupric chloride.

3. The process of claim 1 wherein the catalyst is cuprous chloride.

4. The process of claim 1 wherein the promotor is calcium hydroxide.

5. The process of claim 1 wherein the promoted, catalytic reaction is conducted in an acetonitrile solvent system.

6. The process of claim 5 wherein the catalyst is cupric chloride.

7. The process of claim 5 wherein the catalyst is cuprous chloride.

8. The process of claim 5 wherein the promoter is a Group II A metal hydroxide.

9. The process of claim 8 wherein the promoter is calcium hydroxide.

10. The process of claim 5 wherein the catalyst is CuCl and the promoter is an oxide of a Group II A metal.

11. The process of claim 10 wherein the promoter is beryllium oxide.

12. The process of claim 10 wherein the promoter is calcium oxide.

13. The process of claim 1 wherein the phenol is an alkyl phenol.

14. The process of claim 13 wherein the alkyl phenol is o-cresol or m-cresol.

15. The process of claim 13 wherein the alkyl phenol is a di-methyl phenol.

16. The process of claim 13 wherein the alkyl phenol is a di-tert-butyl phenol.

17. The process of claim 13 wherein the alkyl phenol is o-t-butylphenol.

* * * * *